(12) United States Patent
Martinez Force et al.

(10) Patent No.: US 7,141,267 B2
(45) Date of Patent: Nov. 28, 2006

(54) HIGH OLEIC/HIGH STEARIC SUNFLOWER OILS

(75) Inventors: Enrique Martinez Force, Sevilla (ES); Juan Munoz-Ruz, Cordoba (ES); Jose M. Fernandez Martinez, Cordoba (ES); Rafael Garces, Sevilla (ES)

(73) Assignee: Consejo Superior de Investigaciones Cientificas (CSIC), Sevilla (ES)

(*) Notice: Subject to any disclaimer, the term of this patent is extended or adjusted under 35 U.S.C. 154(b) by 620 days.

(21) Appl. No.: 10/607,803

(22) Filed: Jun. 26, 2003

(65) Prior Publication Data

US 2004/0088758 A1    May 6, 2004

Related U.S. Application Data

(62) Division of application No. 10/021,985, filed on Dec. 13, 2001, now Pat. No. 6,770,803, which is a division of application No. 09/326,501, filed on Jun. 4, 1999, now Pat. No. 6,388,113.

(51) Int. Cl.
     *A23L 1/36* (2006.01)
(52) U.S. Cl. .................................... 426/629; 426/622
(58) Field of Classification Search ................ 426/629, 426/622; 800/264, 322
     See application file for complete search history.

(56) References Cited

U.S. PATENT DOCUMENTS

| | | | |
|---|---|---|---|
| 4,627,192 A | 12/1986 | Fick | |
| 5,147,792 A | 9/1992 | Perchorowicz et al. | |
| 5,298,421 A | 3/1994 | Davies et al. | |
| 5,304,481 A | 4/1994 | Davies et al. | |
| 5,344,771 A | 9/1994 | Davies et al. | |
| 5,443,974 A | 8/1995 | Hitz et al. | |
| 5,558,871 A | 9/1996 | Griat et al. | |
| 5,795,969 A | 8/1998 | Fehr et al. | |
| 5,850,026 A | 12/1998 | DeBonte et al. | |
| 5,885,643 A | 3/1999 | Kodali et al. | |

FOREIGN PATENT DOCUMENTS

| | | |
|---|---|---|
| DE | 3831516 A1 | 3/1990 |
| EP | 0 561 569 A2 | 9/1993 |
| WO | WO 89/03419 A1 | 4/1989 |
| WO | WO 91/16421 A1 | 10/1991 |
| WO | WO 92/11373 A1 | 7/1992 |
| WO | WO 92/20236 A1 | 11/1992 |
| WO | WO 93/18158 A1 | 9/1993 |
| WO | WO 95/20313 A1 | 8/1995 |
| WO | WO 96/06936 A1 | 3/1996 |
| WO | WO 97/12047 A1 | 4/1997 |

OTHER PUBLICATIONS

Ruiz-Gutierrez, V., et al., "Composition of Human VLDL Triacylglycerols After Ingestion of Olive Oil and High Oleic Sunflower Oil," *Journal of Nutrition* 128(3):570-576, 1998 (abstract only).

Alvarez-Ortega, R., et al., "Characterization of Polar and Nonpolar Seed Lipid Classes From Highly Saturated Fatty Acid Sunflower Mutants," *Lipids* 32(8):833-837, 1997 (abstract only).

Wen-Hsiung, L., and Y.-C Chi, "Interesterifaction of Vegetable Oils Using an Immobilized Sn-1, 3-Specific Lipase Adsorbed on Solid Carriers," *Journal of Chinese Agricultural Chemical Society* 35(4):355-364, 1997 (abstract only).

Marquez-Ruiz, G., et al., "Thermoxidative Stability of Triacylglycerols From Mutant Sunflower Seeds," *Journal of the American Oil Chemists' Society* 76(10):1169-1174, 1999 (abstract only).

Martínez-Force, E., and R. Garcés, "New Oilseed Varieties With Modified Fatty Acid Composition in the Oil," *Trends in Agronomy* 2:13-21, 1999.

Osorio, J., et al., "Mutant Sunflowers With High Concentration of Saturated Fatty Acids in the Oil," *Crop Science* 35(3):739-742, 1995.

Garcés, R., and M. Mancha, "One-Step Lipid Extraction and Fatty Acid Methyl Esters Preparation From Fresh Plant Tissues," *Analytical Biochemistry* 211:139-143, 1993.

Rock, C.O., et al., "Preparative Enzymatic Syntheses of Acyl-Acyl Carrier Protein," *Methods in Enzymology* 72:397-403, 1981.

Facciotti, M.T., et al., "Improved Stearate Phenotype in Transgenic Canola Expressing a Modified Acyl-Acyl Carrier Protein Thioesterase," *Nature Biotechnology* 17:593-597, 1999.

Alvarez-Ortega, R., et al., "Characterization of Polar and Nonpolar Seed Lipid Classes From Highly Saturated Fatty Acid Sunflower Mutants," *Lipids* 32(8):833-837, 1997.

Garcés, R., et al., "Sunflower Mutants With Increased Levels of Palmitic and Stearic Acids in the Oil," *Proceedings of the 14th International Sunflower Conference*, Beijing-Shenyang, P.R. China, Jun. 12-20, 1996, pp. 612-615.

Alvarez-Ortega, R., et al., "Fatty Acid Composition of Different Tissues During High Stearic or High Palmitic Sunflower Mutants Germination," in J.P. Williams et al. (eds.), *Physiology, Biochemistry and Molecular Biology of Plant Lipids*, Kluwer Academic Publishers, Dordrecht, The Netherlands, 1997, pp. 322-324.

(Continued)

*Primary Examiner*—Keith Hendricks
(74) *Attorney, Agent, or Firm*—Christensen O'Connor Johnson Kindness PLLC

(57) ABSTRACT

Meal from sunflower plants that produce seeds with an extractable oil having an oleic acid content of more than 40% by weight and a stearic acid content of more than 12% by weight is disclosed.

6 Claims, 3 Drawing Sheets

OTHER PUBLICATIONS

Cantisán, S., et al., "Maturation Changes and Temperature Effect on Fatty Acid Composition in Developing High Saturated Sunflower (*Helianthus annuus*) Seeds," Advances in Plant Lipids Research, *Proceedings of the 13th International Symposium on Plant Lipids*, Sevilla, Spain, Jul. 1998, pp. 125-130.

Martínez-Force, J.M., et al., "Inheritance of High Stearic Acid Content in the Seed Oil of Sunflower," Advances in Plant Lipids Research, *Proceedings of the 13th International Symposium on Plant Lipids*, Sevilla, Spain, Jul. 1998, pp. 134-136.

Martínez-Force, E., et al., "Fatty Acid Composition in Developing High Saturated Sunflower (*Helianthus annuus*) Seeds: Maturation Changes and Temperature," *Journal of Agricultural and Food Chemistry 46*(9):3577-3582, 1998.

Garcés, R., et al., "Sunflower Mutants with Altered Fatty Acid Composition in the Seed Oil," in J.-C. Kader et al. (eds.), *Plant Lipid Metabolism*, Kluwer Academic Publishers, Dordrecht, The Netherlands, 1995, pp. 512-514.

Cantisán, S., et al., "Lipid Characterization in Vegetative Tissues of High Saturated Fatty Acid Sunflower Mutants," *Journal of Agricultural and Food Chemistry 47*(1):78-82, 1999.

Hawkins, D.J., and J.C. Kridl, "Characterization of Acyl-ACP Thioesterases of Mangosteen (*Garcinia mangostana*) Seed and High Levels of Stearate Production in Transgenic Canola," *Plant Journal 13*(6):743-752, 1998.

HIGH OLEIC/HIGH STEARIC SUNFLOWER OILS

This application is a division of application Ser. No. 10/021,985, filed Dec. 13, 2001 (now U.S. Pat. No. 6,770,803), which is a division of application Ser. No. 09/326,501, filed Jun. 4, 1999 (now U.S. Pat. No. 6,388,113).

FIELD OF THE INVENTION

The present invention relates to transgenic and non-transgenic plants that produce oil having high levels of saturated fatty acids and medium to high levels of oleic acid. More specifically the invention relates to a sunflower plant, seed and the extractable oil having increased stearic acid content and increased oleic acid content relative to the normal sunflower oil level of stearic acid and oleic acid.

BACKGROUND OF THE INVENTION

Sunflowers (*Helianthus annuus*) are cultivated for the seeds. Seeds have two principal uses. Seeds are used as confectionery seeds but much more importantly for extraction of oil formed within the sunflower seed. In the endogenous oil are a number of fatty acids. The total fatty acid content is given for 3 types of sunflowers: normal, high oleic and high palmitic. These contents are listed below. The saturated or unsaturated fatty acid is given as a percentage of weight relative to the total fatty acid content.

TABLE 1

| FATTY ACIDS | CARBON CHAIN | PERCENT WEIGHT |
|---|---|---|
| SATURATED ACIDS | | |
| Palmitic | C16:0 | 5%–7% = (normal) |
| | | 2%–5% = (high oleic) |
| | | 22%–40% = (high palmitic) |
| Stearic | C18:0 | <10% but usually 3%–7% (normal, high oleic, high palmitic) |
| UNSATURATED ACIDS | | |
| Oleic | C18:1 | 17%–30% = (normal) |
| | | 9%–12% = (high palmitic) |
| | | 75%–90% = (high oleic) |
| Linoleic | C18:2 | 50%–70% = (normal high palmitic) |
| | | (high oleic) = 2%–10% |

As table 1 indicates a number of different fatty acid distributions in sunflower oil are known. The table gives the wild type or normal sunflower oil as having a fatty acid distribution of the principle saturates of C16:0 levels of 5%–7%, C18:0 levels of <10%, and of the principle unsaturates of C18:1 levels of 17%–20% and C18:2 levels of 50%–70%. Presently, high oleic and high palmitic are known sunflower oils with changed saturate, unsaturated fatty acid profiles.

The industry has been using both transgenic approaches and mutation approaches to alter the saturate, unsaturated fatty acid profiles in the fatty acid biosynthesis pathway. The percentage of saturated and unsaturated fatty acid present in an altered oil reflect the oil's chemical and physical traits. The chemical and physical traits of the oil are altered to form either more useful oil for the industry and/or a healthier oil for the end user.

The last twenty years of sunflower research has produced a healthier oil in high oleic sunflower oil. This research has resulted in the commercial availability of sunflowers having high concentrations of oleic acids (C18:1) percentage by weight based in the total fatty acid content of the sunflower oil. Early Russian research into increasing oleic levels in sunflower seeds used mutagenesis to form Pervenets sunflowers having elevated oleic acid levels. Such oleic sunflower material is available to the public. Much, if not all, of the high oleic sunflower germplasm available today is the descendants of the early Russian lines resulting from that research. Commercially available high oleic sunflower seed includes for example, sunflower variety, Pioneer Hybrid 6661, which is marketed as producing a seed storage oil having a fatty acid composition that includes 85% oleate.

The availability of other high oleic sunflower seed is listed within a number of patent documents. For example, there is intellectual property describing high oleic lines which is believed to be based on the Russian Pervenets sunflowers in U.S. Pat. No. 4,627,192 and Re-examination certificate B1 4,627,192, issued Oct. 17, 1995, and U.S. Pat. No. 4,743,402 and Re-examination certificate B1 4,743,402, issued Apr. 8, 1997, to Flick. These patents list a number of sunflower varieties that are commercially available for breeding purposes that can be licensed under the Fick patents through a company called A.C. Humko. Additionally, the Fick U.S. Pat. No. 4,627,192 indicates that oleic seeds of Sigco 41A, 41b, 853R, 4117b, 273W and 416R are available from the Lubrizol Corporation, 29400 Lakewood Blvd., Wickliffe, Ohio (USA) 44092.

In addition to the research, which resulted in increased oleic acid in sunflower oil, there has also been research on increasing the overall industrial usefulness of sunflower oil usually addressed by increasing the level of the saturated fatty acids in oil. Increasing the saturated fatty acids produces an oil that is more suitable for use in the production of margarine, shortening, other food products, and cosmetics by decreasing the need for substantial amounts of hydrogenation.

Some of this type of research is outlined in *Osorio* et al., in *Crop Sci.* 35:739–42(1995). This article describes sunflower seeds developed by traditional breeding and mutagenesis to produce seeds with a high stearate content. This type of research is also outlined in PCT application number EP95/00369 which is entitled "Sunflower seeds and oil having a high stearic acid content". This application teaches, as its name implies, a sunflower oil with increased stearic acid content. One way to obtain this oil is by treating parent seed with a mutagenic agent to induce one or more mutations in the stearic acid biosynthesis pathway. This process resulted in an increased production of stearic acid in the sunflower oil in a range between 12% and up to 35% by weight of stearic acid related to the total amount of fatty acid in the oil. High stearic acid producing seeds discussed in this patent are under deposit in the American Type Culture Collection (ATCC). Sunflower seeds identified as "CAS-3" have an average stearic acid content of 25% by weight, related to the total amount of fatty acids in the oil. These seeds were deposited on Dec. 14, 1994, with the American Type Culture Collection, 12301 Parklawn Drive, Rockville, Md. 20852, U.S.A., under deposit accession number ATCC 75968. Sunflower seeds identified as "CAS-4" having an average stearic acid content of 15% by weight, related to the total amount of fatty acids in the oil, were deposited on Dec. 14, 1994, with the American Type Culture Collection, 12301 Parklawn Drive, Rockville, Md. 20852, U.S.A., under deposit accession number ATCC 75969.

This application PCT/EP/00369 suggests that oil from high stearic lines could be combined with oil from high oleic lines for certain industrial uses. Unfortunately, although this combination of two oils is useful in many instances, there remains a need for a seed that produces high levels of both stearic and oleic fatty acids in the same oil, particularly since the levels of linoleic acid produced by these stearic acid lines may tend to produce a less desirable profile of fatty acids, than would be produced by a hybrid producing high stearic, high oleic acid.

Traditional breeding and mutagenesis has not been the only tool used to form seeds producing oil with different fatty acid profiles. Increases in stearic acid in oil bearing plants have also been addressed by the introduction of transgenes into the germplasm, to alter the fatty acid biosynthesis pathway of the vegetable oil. The fatty acid biosynthesis in vegetable oil, but more particularly sunflower oil, includes the biosynthesis of basically two saturates palmitate, stearate and two unsaturates oleate and linoleate. To give a simplified description of the biosynthesis pathway, it is sufficient to say; that palmitate (C16:0) is by enzymatic action chemically modified to form stearate (C18:0), which by enzymatic action is modified to produce oleate (C18:1), that is further modified to form linoleate (C18:2), some minor amounts of araquic (C20:0) and behenic (C22:0) acids are also formed from stearate. In ojiseeds the stearoyl-ACP desaturase is the enzymatic action which introduces the first double bond on stearoyl-ACP to form oleoyl-ACP. Thus, this is an enzyme that assists in the determination of the unsaturation in the C18 length fatty acids.

In U.S. Pat. No. 5,443,974 the inhibition of canola enzyme stearoyl-ACP desaturase was described. The stearate levels were increased but the levels of palmitate were basically unaffected. Inhibition of the plant enzyme stearoyl-ACP desaturase in canola was also reported by Knutzon et al., *Proc. Nat'l Aca., Sci. USA* 89:2624–28 (1992). These results showed an increase in the level of stearate produced in the canola seed. The research also showed that inhibition by antisense in seeds of canola and soybean, respectively showed increased stearate. When a plasmid containing a gene encoding for stearoyl-ACP desaturase was placed in canola, this inhibition resulted in both an increase in stearic acid and unfortunately a reduction in the oleate. However, in the soybean this inhibition of stearate resulted in a less dramatic reduction of the oleate. This slower decrease in oleate however may have been a function of the small initial levels of oleate in the soybean. The fatty acid pathway in most oilseed plants appears to be resistant to maintaining both oleic and stearic at elevated levels.

Additionally, Pioneer Hi-Bred International, Inc., has increased the levels of both stearic acid and palmitic acid in sunflowers through the inhibition of the plant enzyme stearoyl-ACP desaturase. This research was surprising in light of other transformations in other plants that indicated that this enzyme would not affect palmitic acid levels only stearic acid levels. Unfortunately, palmitic oil is not viewed as being a healthy oil. This research is indicated in PCT/US97/01419.

Pioneer Hi-Bred International, Inc. taught in PCT/US96/09486 that sunflower oil levels of both palmitic and oleic acids could be increased. Sunflower seeds having increased levels of palmitic 21–23% and oleic 61% were deposited in the ATCC as 93PMOL040G and 93PMOL040F in the American Type Culture Collection 12301 Parklawn Drive, Rockville Md. 20852, U.S.A. having Accession No. 97159 and 97158 respectively. The patent application teaches a sunflower oil that is liquid at room temperature. But the increased palmitic fatty acid level in the Pioneer invention, is alleged to allow the oil to be used in shortening and in margarine with relatively low level of hydrogenation, which leads to a relatively low level of trans-fatty acids in the resulting product. However the commercial value may be questioned as palmitic oil is not viewed as being a very healthy oil. Thus margarine made with this oil may be substantially less desirable than margarine made with a healthier combination of fatty acids (i.e. stearic acid).

There remains a need for a sunflower oil which is healthy and useful for industrial purposes. There is a need for a sunflower oil that has a balance of good saturates and good unsaturates. There also remains a need for a sunflower oil that is high in unsaturates but has sufficient saturates to be used for margarines or hardstock without high levels of hydrogenation which lead to no trans-fatty acids in the resulting product. There remains a need for a sunflower plant that can produce seed containing oil which is high in oleic acid and in stearic acid with reduced linoleic levels.

It is an object of the present invention to provide novel sunflower plants which form seeds which contain an endogenous oil wherein the levels of stearic acid (C:18) and oleic acid (C:18:1) are provided in an a typical combination.

It is further an object of the present invention to provide sunflower plants, seeds and oil obtainable from the seeds that has an oleic content of more than 40% by weight of oleic acid and a stearic acid content of more than 18% by weight.

It is further an object of the present invention to provide sunflower seed and lines which when crossed form hybrids having the genetic characteristics to yield high levels of oleic acid and high levels of stearic acid content in the oil as compared to oil obtained from wild type seeds.

It is an object of the present invention to provide F1 hybrid seeds having the genetic characters to yield plants which form seeds characterised by high levels of oleic acid and high levels of stearic acid content as compared to oil obtained from wild type seeds.

The invention further relates to sunflower plants produced from seeds according to the invention that can produce parent lines with high stearic acid and high oleic acid levels in their oil. This applies to the seeds and the progeny therefrom obtained after crossing the mutants of the invention with each other or with other germplasm having a desirable characteristic.

It is another object of the present invention to produce sunflower plants that may be used in breeding programs aimed at the production of open pollinated or inbred or hybrids having acceptable agronomic traits that are useful in the field environment.

DEFINITIONS

Figure 1:
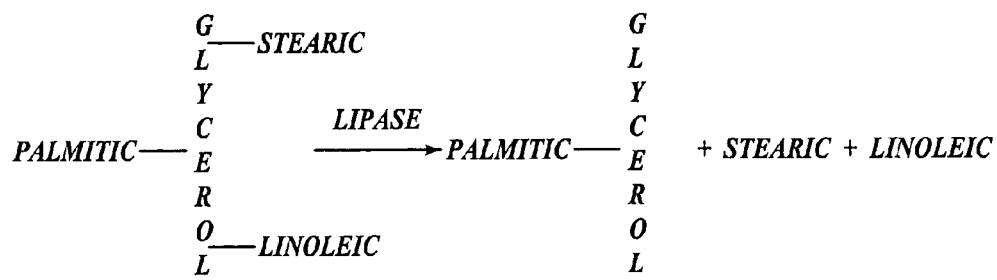
FIG. 1—TAG shown hydrolysis of the triacylgycerols by the lipase.

SUNFLOWER plant shall mean all *Helianthus annuus* plant and cell parts including pollen, kernel, oil, embryo, stalk, head, roots, cells, meristems, ovule, anthers, microspores, embryos, DNA, RNA, petals, seeds, and the like and protoplasts, callus or suspensions of any of the above.

15DAF shall mean 15 days after flowering.

HOLT shall mean a sunflower having high to medium-high (40%–90%) oleic acid levels in the oil when compared to normal, wildtype sunflower seed (oleic acid levels of 17%–20%) levels wherein there is low levels of thioesterase activity.

TOTAL FATTY ACID CONTENT refers to the sum of C16:0, 18:0, 18:1, 18:2, 20:0, 22;0 and the traces of other like fatty acids as determined simultaneously in the seed sample.

HOHT shall mean a sunflower having high to medium-high (40%–90%) oleic acid levels in the oil when compared to normal, wildtype sunflower seed (oleic acid levels of 17%–20%) levels wherein there is high levels of thioesterase activity.

LOW LEVELS OF THIOESTERASE ACTIVITY shall mean levels of stearoyl-ACP thioesterase activity at DAF15 which are lower than 10% of the activity over oleoyl-ACP, this permits an exportation out of the plastid of a maximum of less than 12% of stearic acid with respect to the total fatty acids synthesised by the plastid.

HIGH LEVELS OF THIOESTERASE ACTIVITY shall mean levels of stearoyl-ACP thioesterase activity at DAF15 which are higher than 10% of the activity over oleoyl-ACP, this permits an exportation out of the plastid of a minimum of 12% of stearic acid with respect to the total fatty acids synthesised by the plastid.

SUMMARY OF THE INVENTION

The present invention broadly relates to high oleic/high stearic vegetable oils. More specifically the present invention relates to the sunflower seeds, the sunflower plants, sunflower meal or crushed seeds, oil obtainable from the seeds and the extracted endogenous sunflower oil, which has a fatty acid profile high in oleic acid and in stearic acid. Still more specifically this invention has a fatty acid profile that also has preferably less than 25 percent linoleic and more preferably less than 10 percent linoleic. Additionally the profile of the invention is often selected to have palmitic levels below 21%.

In the broad scope the invention the sunflower seeds, the sunflower plants, sunflower meal or crushed seeds obtainable from the seeds and the extracted sunflower oil contain or produce an oleic acid content of more than 40% weight and a stearic acid content of more than 12% weight based on the total fatty acid content of the oil. The more preferred invention for certain spread uses has oil and the seeds containing the oil which contain an oleic acid content that is from 55 to 75% weight relative to total fatty acid content and a stearic acid content from 15 to 40% weight relative to total fatty acid content. The scope of the invention includes oil and the seeds containing the oil plants capable of forming such oils which have a total level of saturated fatty acids of at least 20 wt %.

The sunflower seed containing oil is usually selected to have at least 90% weight of the saturated fatty acid groups in the 1 and/or 3 position as indicated in Table 6. In some instances the invention can have from 95 to 100% weight of the saturated fatty acid groups in the 1 and/or 3 position. The present invention also includes a sunflower plant capable of producing the sunflower seeds containing such oils.

The present invention also covers the method of obtaining a sunflower oil having an oleic acid content of more than 40% weight and a stearic acid content of more than 12% weight based on the total fatty acid content of the oil by extracting oil from the seeds. The method includes an extraction process which does not involve a substantial modification of the sunflower oil. Additionally, in the process of extraction of the oil from the seed there is no substantial chemical or physical modification nor enzymatic rearrangement taking place and no substantial hardening of the oil.

The present invention also includes food products comprising oil obtainable from seeds having an oleic acid content of more than 40% weight and a stearic acid content of more than 12% weight based on the total fatty acid content of the oil. Food products that are particularly useful for this type of oil include spreads, margarine's, shortenings, sauces, ice-cream, soups, bakery products, confectionery products, and the like. In these food products the level of sunflower oil is from 3 to 100% weight relative to the total oil weight in the product. When used to form a spread according to the present invention the sunflower oil is used as a hardstock at levels of 5 to 20% by weight.

The present invention also encompasses cosmetic products comprising a sunflower oil, the oil having an oleic acid content of more than 40% weight and a stearic acid content of more than 12% weight based on the total fatty acid content of the oil. These cosmetic products can contain levels of sunflower oil from 3 to 100% by weight. Some examples of these cosmetic products would include creams, lotions, lipsticks, soap bars and skin or hair oils.

The present invention also includes a process for selecting *Helianthus annuus* plants, capable of producing the seeds having the desired oil. The steps of the method are a) selecting a number of *Helianthus annuus* plants, collecting therefrom the seeds, which have a mutation induced by a mutagenic agent or an introduced transgene such that the oil in the seed has a stearic acid content of at least 12% weight based on the oil present in the seed; (b) selecting a number of *Helianthus annuus* plants, collecting therefrom the seeds, which express an oleic acid content of at least 40% weight based on the oil present in the seed and a high level of thioesterase activity (c) crossing the plants grown from the seeds of (a) and (b) and, harvesting the F1 seed progeny.

Additional steps include the steps of:(d) planting of the seeds or embryos rescue of the embryos of the F1 progeny obtained to form F2 segregating seeds;(e) selecting from the F2 seeds which developed plants, those plants which produce seeds having an oleic acid content of more than 40 wt % and a stearic acid content of more than 12 wt % based on the total fatty acid content of the oil, optionally selfing the selected plant to form true breeding inbreds.

The present invention also includes the process for producing F1 hybrid seed. The steps of the method are a) planting seed of two inbreds having high oleic acid content of at least 40% and high levels of thioesterase activity, one of which may be male sterile, b) crossing the two inbreds, and c) harvesting the F1 seed capable of producing F2 seed with a 40% oleic acid content and a 12% stearic acid content.

DESCRIPTION OF THE INVENTION

The present invention encompasses a vegetable oil with a new and unique fatty acid composition produced in easy to grow crops. The preferred crop is sunflower. However, mutation and/or transformation to produce the derived vegetable oil could likewise modify other crops. These crops would include at least *Brassicas*, peanuts, palms and other oil producing plants. The crop should be readily transformable and/or susceptible to mutagenically induced oil changes. Rape seed meets all these requirements as does sunflower, these crops are presently some of the most useful crops for production of this new and unique fatty acid composition in the oil of their seeds.

The industrial use for oil which are capable of being extracted from the seeds is determined by its fatty acid composition. Table 2 shows the fatty acid composition and other properties of some fats and oils. The oils obtained from seeds cultivated in temperate climate (sunflower, soybean, rape seed, etc.) have mainly unsaturated fatty acids, like linoleic and oleic acids, so they are liquid and primarily used for cooking, salad dressing, etc. Saturated fatty acids are solid at room temperature and referred to as fats. These saturated fatty acid are mainly obtained from animals (margarine, lard, etc.), some tropical trees (cacao, palm) or one chemically modified (hydrogenation and transesterification) liquid vegetable oils. These modified liquid vegetable oils have mainly saturated (palmitic or stearic acids) or chemically modified fatty acids (trans fatty acids) with high melting points.

which are mainly excreted. But fatty acids in position 2 form a molecule of monoacylglycerol, which is easily absorbed into the body, raising LDL.

Therefore, vegetable oils are modified to form hard fats. These vegetable oils are hydrogenated and/or transesterified to increase the percentage of saturated fatty acids. However, the resulting oils are unfortunately not necessarily healthier fats. The hydrogenation process produces "trans fatty" acids that probably are even less healthy than saturated fatty acids, while the transesterification process randomly exchanges the fatty acids within the three positions. Thus, neither of the two chemical modification works well to truly form healthy fats.

But not all saturated fats are unhealthy, it have been demonstrated that cocoa butter, that has around 60% of saturated fatty acids, the rest being mainly oleic acid, does not raise serum cholesterol. This is due to two main reasons, one is that only 4% of the saturated fatty acids are in position 2 and the other is the principal saturated fatty acid is stearic acid. Stearic acid does not appear to have a negative effect on serum cholesterol, and is considered healthier than palmitic acid, which is the main saturated fatty acid of commod-

TABLE 2

Total fatty acid, and other special properties, like trans fatty acid and saturated fatty acid at position 2 of the TAG molecule, of several oils and fats. In the column labelled others are palmitoleic acid in the case of lard and olive oil and also fatty acids shorter than 12 carbons in the butter. Minor amounts (<2%) of other fatty acids are also present in some oils.

| Oil or fat | Fatty acid composition (%) | | | | | | Properties | |
|---|---|---|---|---|---|---|---|---|
| | Others | Myristic | Palmitic | Stearic | Oleic | Linoleic | Trans | Saturated |
| Lard | 3 | 2 | 25 | 12 | 45 | 10 | 1 | 79 |
| Butter | 14 | 10 | 26 | 12 | 28 | 3 | 3 | 84 |
| Margarine | | | 10 | 7 | 46 | 34 | 23 | |
| Palm Oil | | 1 | 45 | 5 | 39 | 9 | | 18 |
| Olive Oil | 1 | | 14 | 3 | 71 | 10 | | 2 |
| Cocoa Butter | | | 26 | 35 | 35 | 3 | | 4 |
| Normal Sunflower | | | 7 | 5 | 30 | 57 | | 1 |
| High oleic sunflower | | | 5 | 4 | 88 | 2 | | 1 |

The fats are needed by the food industry to make margarine, shortening, bakery, confectionery, snacks, etc. The industry uses the fat for their physical properties. Fats do not readily melt at room temperature, can be spread and does not stick. Fats also have greater stability, which is a resistance to oxidation at room temperatures.

Unfortunately, fats also have negative nutritional properties. Many fats raise the levels of bad serum cholesterol (low-density lipoprotein, LDL) in blood. The principal component of fats and oils is triacylglycerol (TAG), normally making up more than 95% of the fat or oil. Three fatty acids are bound to a molecule of glycerol to make the TAG. These fatty acids are either saturated or unsaturated. Fat having negative nutritional properties is due to having most of the saturated fatty acids in the position 2 of the TAG molecule (FIG. 1). Most vegetable fats and oils which do not raise LDL have little saturated fatty acids in this position. The fatty acids in positions 1 and 3 are liberated as free fatty acids by lipase in digestion, if these fatty acids are saturated they form insoluble salts with calcium and magnesium, ity fats. Additionally, the 35% of oleic acid content in the cocoa butter also provides healthy properties to the fat.

There remains a need of the industry for a vegetable oil (fat) with high stearic acid (as the saturated fatty acid) and elevated oleic acid (as unsaturated fatty acid) content that will resolve the actual fat problems, preferably with the stearic acid in the 1 and 3 position of TAG. To that end the present invention can be selected to have at least 90 w/w % of saturated fatty acids in the 1 and/or 3 position. In the more preferred embodiments of the invention there is 95–100% w/w % of saturated fatty acids in the 1 and/or 3 position. Thus the present invention produces an oil/fat that is addressing the industry's need for healthier fats.

The main characteristics of modified plants, its seeds and the oil capable of being extracted from these seeds according to the invention are the production of a vegetable oil with increased oleic acid (beyond normal Sunflowers in Table 1) and with a stearic acid content of 12% and above. Even more specifically the percentage stearic acid content is between 15% and 40% by weight and even more specifically the invention can be selected to have a stearic acid content of between 20% and 35%, an oleic acid content of preferably above 40%. More specifically an oleic acid content of the oil of the present invention is between 50% and 80% by weight. Yet, more specifically the present invention has the high stearic acid and the high oleic acid content of between 55% and 75% by weight relative to the total fatty acid content. Additionally, the invention with high oleic and high stearic acid also contains high levels of thioesterase activity. The linoleic acid content of the present invention is usually selected to be less than 25% by weight related to the total amount of fatty acids in the oil. The seeds according to the invention can be selected to have at least 20% by weight total level of saturated fatty acids relative to the total fatty acid content for the oil.

Originally it was believed that crossing the prior art high oleic lines with the prior art high stearic lines would produce an inbred line having high oleic and high stearic properties. Unfortunately, this has proved extremely difficult. The prior art high stearic acid content lines, which were selected-after mutagenesis, like CAS-3, evidenced low oleic content. Likewise, most high oleic varieties evidenced low stearic acid content.

Figure 2:
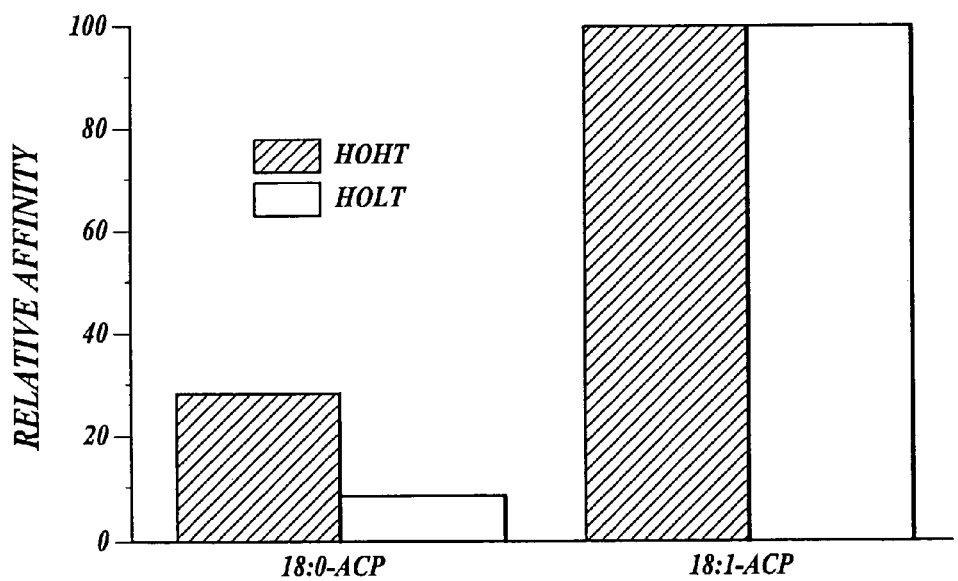
FIG. 2—is elevated thioesterase shown as the relative affinity of the thioesterase on stearoyl-ACP and oleoyl-ACP of HOHT and HOLT.

We have discovered that the selection process for very high oleic material, particularly in sunflower, selects against stearic acid generally. Thus the present invention is possible due to the discovery that to form a plant such as a sunflower plant, which is capable of producing the desired oil, the starting material should contain a third characteristic beyond high oleic and high stearic, it should evidence elevated thioesterase activity over the stearoyl-ACP as indicated in FIG. 2.

Figure 3:
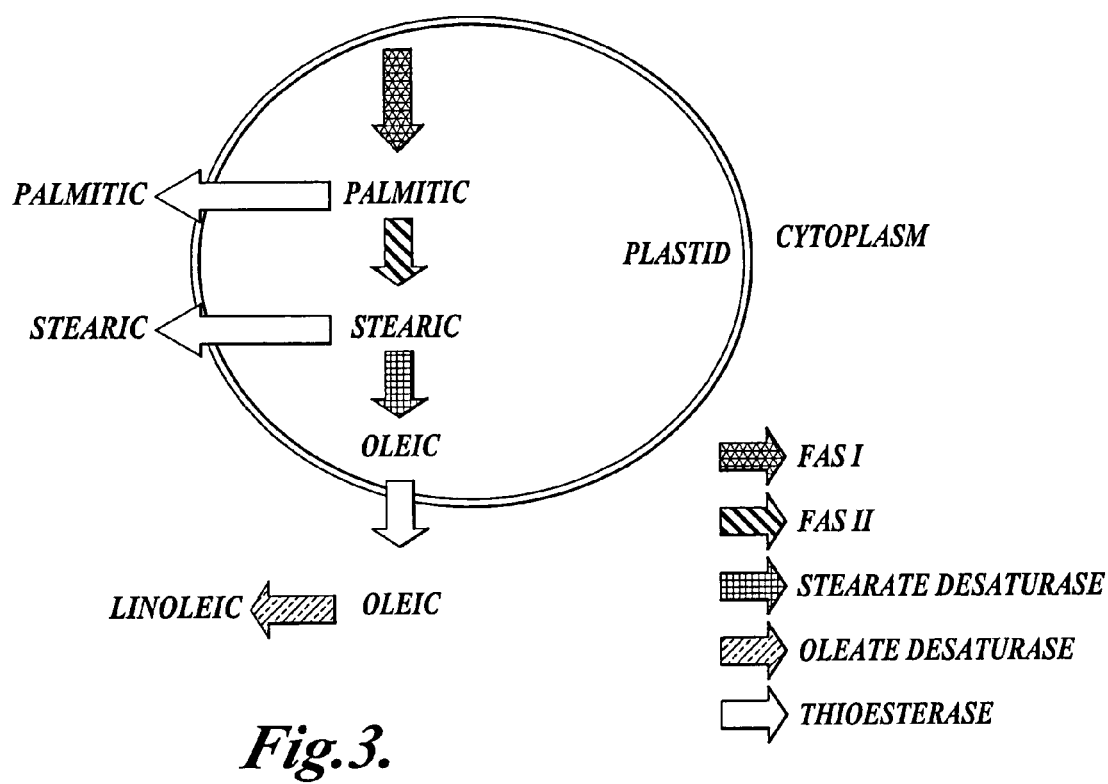
FIG. 3—plastid showing the fatty acid biosynthesis in oilseeds

To assist in the understanding of the role of thioesterase activity within the present invention, a general review of the fatty acid biosynthesis in sunflower is helpful. The seed fatty acid biosynthesis occurs inside the plastid (FIG. 3). The fatty acids within the plastid remain covalently bound to the acyl carrier protein (ACP) during successive cycles of extension (synthesis of palmitic and stearic acids) and desaturation (conversion of stearic acid to oleic acid). The major products of this biosynthetic process are palmitoyl-ACP, stearoyl-ACP and oleoyl-ACP. A series of cycling reactions catalysed by the enzymatic complex FAS I produce the palmitoyl-ACP that have 16 carbons. A second enzymatic complex called FAS II elongates the palmitoyl-ACP to stearoyl-ACP (18 carbons), that is further modify by the stearate desaturase to produce oleoyl-ACP. These are the three main fatty acids synthesised by the plastid. These are separated from the ACP by the action of the thioesterase (Acyl-ACP thioesterase catalyse the hydrolysis of acyl thioesters) and then exported out of the plastid in to the cytoplasm where the synthesis of triacylglycerides takes place. Later the oleic acid can be desaturated to linoleic and linolenic acids. The synthesis of TAG (storage oil) is produced in the cytoplasm using the pool of fatty acids in the cytoplasm, and this pool is made from the fatty acids exported from the plastid and the linoleic acid made by desaturation. So, the fatty acid composition of TAG is determined by the plastid exported fatty acids plus the linoleic acid produced in the cytoplasm.

The present invention, a vegetable oil that is rich in stearic and oleic acids, is formed by altering the standard fatty acid biosynthesis described above. By combining a reduced stearate desaturase activity with a good thioesterase activity on stearoyl-ACP in a high oleic line a vegetable oil rich in stearic and oleic acid is formed according to this invention. The invention accumulates stearoyl-ACP inside the plastid, and the thioesterase over stearoyl-ACP activity exports it out of the plastid. This higher stearic acid content is available for TAG biosynthesis. Later, in the cytoplasm the high oleic character avoids the conversion of oleic acid into linoleic acid.

A plant capable of producing the oil of the present invention may be obtained by two basic methods. The first method is mutagenesis and breeding the second method is transformation and breeding which is discussed later. Regardless of the method, the trait high levels of thioesterase activity should be identified and bred for in the scope of the present invention.

To form the oil of the present invention a plant capable of producing seed having oil containing the high oleic and high stearic acid content must be formed. To achieve this objective a high oleic, high thioesterase line can be crossed with a high stearic line which results after selfing and selection in an inbred that is high oleic and high stearic. This requires two basic elements a high stearic line and a HOHT line. The simplest way to form the present invention is by making sexual crosses of a high stearic line such as CAS-3, with a HOHT sunflower line and selecting for HSHO (a line which produces a seed characterised by high stearic acid and high to medium high oleic acid in the oil). The first basic element CAS-3 is material deposited in the ATCC, the second element is the HOHT.

The first basic element can also be formed by mutation of existing germplasm and screening for the high stearic trait. This can be done according to the teaching of application PCT/EP95/00369. Various mutation methods are detailed in the examples. But briefly one method to form a high stearic acid line treats the parent seeds for 2 hours at room temperature in a solution of 70 mM ethyl methane sulfonate in water, or 2 hours at room temperature with a solution of 2 mM sodium azide in water to form a desired oil trait mutation. The resultant material is selected for the stearic acid trait. The lines are selfed (if necessary) to form a true breeding line.

The HOHT line can be screened and selected from the existing prior art high oleic sunflower lines. The screening would be based on maintaining the high oleic trait and locating the trait for high thioesterase activity and selecting for both traits. Alternatively the second element, HOHT, can be formed by crossing a fixed high oleic line which is HOLT with a line evidencing high levels of thioesterase activity and through selfing and selection throughout several generations, a new HOHT can be formed. A less efficient alternative to forming the HOHT is by mutation, selfing, screening and selection throughout several generations. In this alternative using normal germplasm and mutating it and selecting for either the high oleic trait or the HOHT trait can form the HOHT line. However, since there is a number of high oleic sunflower lines available it should not be necessary to reform a HOHT line from normal germplasm. Screening high oleic lines for high levels of thioesterase activity should be sufficient to locate a HOHT line.

The reason a HOHT line is necessary and the high oleic trait does not appear sufficient is that it have been found that the selection process for very high oleic material selects against stearic generally and also against elevated thioesterase activity over the stearoyl-ACP. Although some high, or more accurately medium-high, oleic lines carry elevated thioesterase activity over the stearoyl-ACP, in general, as the oleic level increases the thioesterase activity decreases. Measuring the thioesterase activity, from lines, having high eighties, and oleic lines, with medium-high levels at sixty, seventy and low eighties of oleic, shows a number of high oleic lines in the medium-high level with good activity over stearoyl-ACP.

Turning to the thioesterase activity over stearoyl-ACP, this activity is used to select the material for use in the development of new inbred line carrying high oleic and stearic traits according to the present invention. During sunflower seed formation, an active period of fatty acid biosynthesis takes place between 12 and 28 DAF. The maximum in vitro acyl-ACP (acyl-carrier-protein) thioesterase activities are found at 15 DAF, preceding the largest accumulation of lipid in the seed (18 DAF). Changes in acyl-ACP thioesterase activity are not only quantitative, but also qualitative, since, although the preferred substrate is always oleoyl-ACP, the affinity for palmitoyl-ACP decreases, whereas that for stearoyl-ACP increases with seed maturation. At 15 DAF the level of thioesterase activity can be measured as shown in the examples to determine which lines should be progressed.

In Table 3 we can see an example of two high oleic lines, the usual high oleic line which has low thioesterase over stearoyl-ACP(HOLT) and the high oleic line with high thioesterase over stearoyl-ACP(HOHT) which has more than twice the thioesterase Vmax over stearoyl-ACP than the usual high oleic line.

TABLE 3

Stearic acid content and thioesterase Vmax over
the stearoyl-ACP at 15 days after flowering seeds from
two high oleic sunflower lines.

| Sunflower line | Stearic acid (%) | V max |
|---|---|---|
| HOHT | 17.8 | 2.03 |
| HOLT | 8.0 | 0.82 |

This HOHT line is deposited with the ATCC at 10801 University Boulevard, Manassas, Va. 20110-2209, on Sep. 7, 1999, and assigned PTA-628. As Table 3 indicates, this line has more stearic acid at 15 days after flowering than the HOLT. This stearic acid level at 15 DAF can also be employed as a rough screening protocol for selecting HOHT lines. The relative affinity of the enzymes over the stearoyl-ACP standardised with respect to the one over oleoyl-ACT are also shown in FIG. 2.

Additionally, the oil obtained from the mature seed of the HOHT also evidences increased stearic acid levels relative to the HOLT line (Table 4).

TABLE 4

Fatty acid composition (%) of seeds from
two high oleic sunflower lines.

Fatty acid composition (%)

| Sunflower line | Palmitic | Stearic | Oleic | Linoleic | Araquic | Behenic |
|---|---|---|---|---|---|---|
| HOHT | 4.3 | 9.7 | 78.5 | 3.9 | 1.0 | 2.6 |
| HOLT | 3.8 | 4.9 | 84.3 | 4.8 | 0.5 | 1.7 |

Commercially and publicly available high oleic material, the deposited material or newly formed mutated high oleic lines produced according to the examples or by other methods of mutation or transformation can be screened according to the procedure outlined in example 4. The selected lines can have an increased thioesterase Vmax on the substrate stearoyl-ACP at 15 DAF having activity levels as indicated in the definition of high levels of thioesterase. The result of finding a HOHT line is that the fatty acid content will most often evidence an increase in the stearic acid level (when compared to a HOLT) in the line while maintaining a high oleic content. It should be noted that the oleic content of these (HOHT) lines is more likely to be in the sixty, seventy or low eighty range versus the high eighties.

Previous to our invention, selecting for high oleic lines selected against this thioesterase activity. Thus when a HOLT (high oleic line with low thioesterase activity) was crossed with or transformed with a high stearic producing trait the stearic level dropped to unacceptably low levels. However, the HOHT line when crossed with the stearic acid line carries the stearic acid level of the CAS 3 in the F2 seed. In contrast the HOLT line decreased the stearic acid level of the CAS 3 in the F2 seed. This is shown in Table 5 where lines of both HOLT and HOHT have been crossed with the high stearic CAS-3 line. Also shown in Table 5 is the fatty acid composition of these lines.

TABLE 5

Fatty acid composition of selected high oleic and
stearic lines, with high and low thioesterase activity
over stearoyl-ACP, after crossing by CAS-3.

Fatty acid composition (%)

| Sunflower line | Palmitic | Stearic | Oleic | Linoleic | Araquic | Behenic |
|---|---|---|---|---|---|---|
| HOHT × CAS-3 | 5.2 | 24.6 | 59.2 | 6.8 | 1.8 | 2.4 |
| HOLT × CAS-3 | 4.3 | 17.4 | 72.1 | 4.0 | 1.3 | 2.8 |

Figure 4:
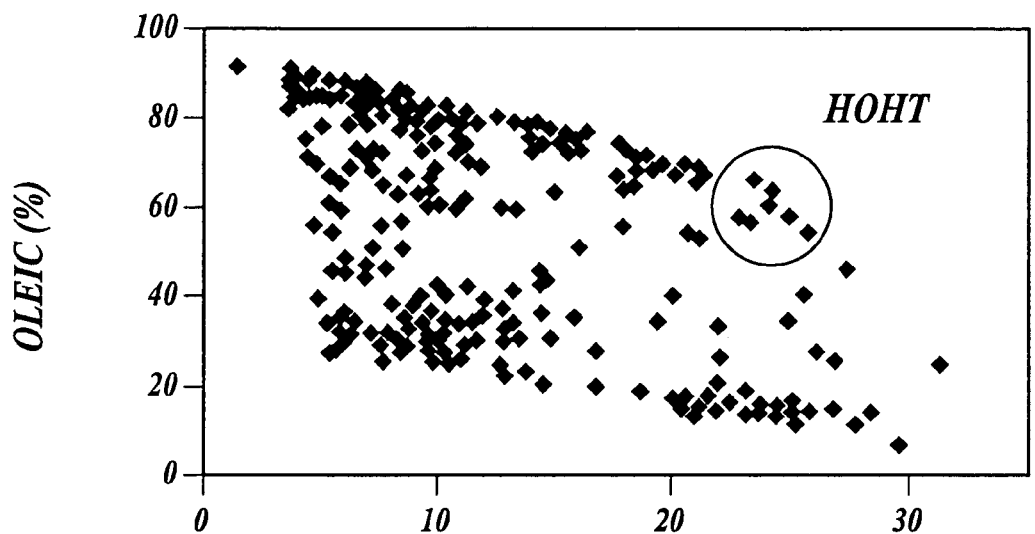
FIG. 4—the F2 segregation for HOHT indicating HOHT progeny
Figure 5:
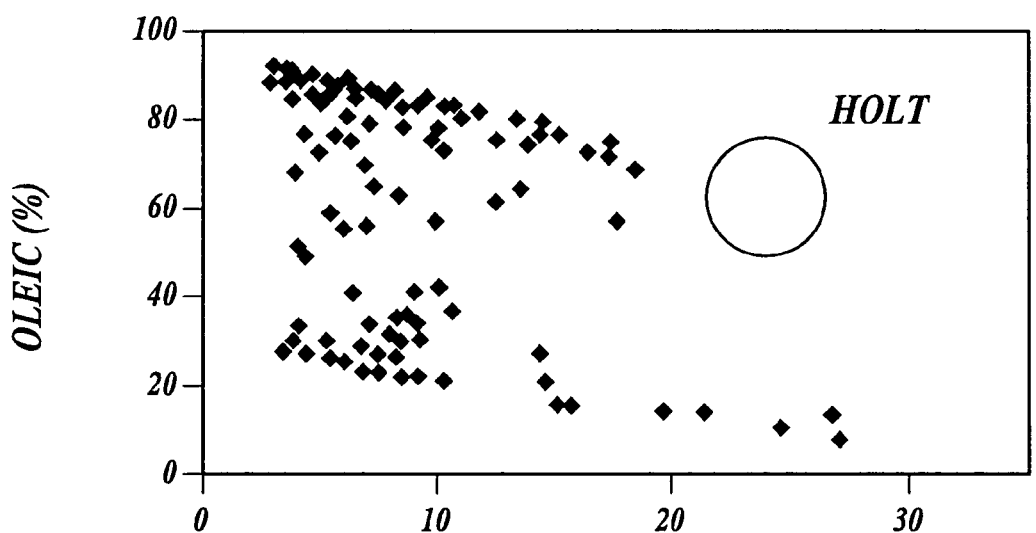
FIG. 5—the F2 segregation for HOLT indicating no HOHT progeny

In FIGS. 4 and 5, the F2 segregation for both high stearic acid content and high oleic acid content of the above lines are shown. The seeds formed form the HOHT × CAS-3 cross which have the higher stearic and oleic acids are within a circle. The line with high thioesterase activity over stearoyl-ACP has these kinds of seeds and the line without this high thioesterase activity have no seeds of this type.

The selected F2 lines are selfed for 5 to 6 generations in isolated conditions to avoid contamination. The resultant generations are selected, based on high oleic, and stearic acid content. Thioesterase activity can be analysed to assist in the selection process. Likewise, marker assisted breeding can be employed to track any or all of the three traits to make the selection process quicker. Various markers such as SSR microsatellite, ASO, RFLP and likewise can be employed. The use of markers is not necessary, as standard tests are known for determining oleic, stearic, and thioesterase activity. However, once identified markers make trait tracking easier and earlier in the plant's life.

The true breeding plants produce an oil having a similar fatty acid composition that the F2 seeds selected with a low content of saturated fatty acid in the 2 position of the TAG molecule (Table 6).

TABLE 6

Fatty acid composition of oil, TAG and Sn positions
of true breeding HSHO plants selected.

Fatty acid composition (mol %)

| | Palmitic | Stearic | Oleic | Lionoleic | Araquic | Behenic |
|---|---|---|---|---|---|---|
| Total oil | 5.5 | 24.9 | 57.8 | 8.2 | 1.7 | 1.8 |
| TAG | 5.6 | 26.1 | 57.6 | 7.4 | 1.6 | 1.7 |
| sn-2 position | 1.7 | 1.9 | 87.4 | 9.0 | n.d. | n.d. |
| sn-1 and 3 position | 7.2 | 33.1 | 46.8 | 7.3 | 2.7 | 2.9 | n.d. = not detected.

As indicted earlier the two basic elements employed to form the present invention can be developed by mutation and breeding or by transformation and breeding. In accordance with the present invention the sunflower plant can evidence the stearic or oleic acid traits by introduction, either presently or in the ancestry of the line, mutation of the genes. A number of mutation methods including irradiation, chemical mutation, and other forms of causing gene deletions or changes can work. Particularly, easy to use are mutagenic agents that result in small changes in the genome such as point mutations.

Alternatively, as mentioned previously there is a second method to produce the stearic or oleic lines in accordance with the present invention, the sunflower plant can evidence the stearic or oleic acid traits by transforming a gene into the plant to produce one or more of the desired traits.

The use of gene sequences to inhibit or promote gene expression is quite well understood. A complete gene sequence, under the control of a promoter that operates effectively in the plant, will generally overexpress the gene product, leading to an amplification of the effect of the protein so produced. Sometimes the gene product is reduced: this phenomenon is termed "co-suppression". Reduction of the gene product is also generally obtained by using a dominant negative mutation, or by reversing the orientation of the gene sequence with respect to the promoter so that it produces "antisense" messenger RNA.

A DNA construct according to the invention may be an "antisense" construct generating "antisense" RNA or a "sense" construct (encoding at least part of the functional protein) generating "sense" RNA. "Antisense RNA" is an RNA sequence which is complementary to a sequence of bases in the corresponding mRNA: complementary in the sense that each base (or the majority of bases) in the antisense sequence (read in the 3' to 5' sense) is capable of pairing with the corresponding base (G with C, A with U) in the mRNA sequence read in the 5' to 3' sense. Such antisense RNA may be produced in the cell by transformation with an appropriate DNA construct arranged to generate a transcript with at least part of its sequence complementary to at least part of the coding strand of the relevant gene (or of a DNA sequence showing substantial homology therewith). "Sense RNA" is an RNA sequence, which is substantially homologous to at least part of the corresponding mRNA sequence. Such sense RNA may be produced in the cell by transformation with an appropriate DNA construct arranged in the normal orientation so as to generate a transcript with a sequence identical to at least part of the coding strand of the relevant gene (or of a DNA sequence showing substantial homology therewith). Suitable sense constructs may be used to inhibit gene expression (as described in International Patent Publication WO91/08299) or a sense construct encoding and expressing the functional protein may be transformed into the plant to over express the protein.

DNA constructs according to the invention may comprise a base sequence at least 10 bases (preferably at least 35 bases) in length for transcription into RNA. There is no theoretical upper limit to the base sequence it may be as long as the relevant mRNA produced by the cell but for convenience it will generally be found suitable to use sequences between 100 and 1000 bases in length. The preparation of such constructs is described in more detail below.

As a source of the DNA base sequence for transcription, a suitable cDNA or genomic DNA or synthetic polynucleotide may be used. The isolation of suitable sequences encoding stearoyl-ACP desaturase from Brassica and Arabidopsis are described in U.S. Pat. No. 5,443,974: similar methods may be used to isolate sequences encoding stearoyl-ACP desaturase from other plants. These may have greater or lesser degrees of homology with sequences encoding stearoyl-ACP desaturase from Arabidopsis. Sequences coding for the whole, or substantially the whole, of the protein may thus be obtained. Suitable lengths of this DNA sequences may be cut out for use by means of restriction enzymes. When using genomic DNA as the source of a partial base sequence for transcription it is possible to use either intron or exon regions or a combination of both.

To obtain constructs suitable for modifying expression of these desaturase in plant cells, the cDNA sequence as found in the protein cDNA or the gene sequence as found in the chromosome of the plant may be used. Recombinant DNA constructs may be made using standard techniques. For example, the DNA sequence for transcription may be obtained by treating a vector containing said sequence with restriction enzymes to cut out the appropriate segment. The DNA sequence for transcription may also be generated by annealing and ligating synthetic oligonucleotides or by using synthetic oligonucleotides in a polymerase chain reaction (PCR) to give suitable restriction sites at each end. The DNA sequence is then cloned into a vector containing upstream promoter and downstream terminator sequences. If antisense DNA is required, the cloning is carried out so that the cut DNA sequence is inverted with respect to its orientation in the strand from which it was cut.

In a construct expressing antisense RNA, the strand that was formerly the template strand becomes the coding strand, and vice versa. The construct will thus encode RNA in a base sequence which is complementary to part or all of the sequence of the protein mRNA. Thus the two RNA strands are complementary not only in their base sequence but also in their orientations (5' to 3').

In a construct expressing sense RNA, the template and coding strands retain the assignments and orientations of the original plant gene. Constructs expressing sense RNA encode RNA with a base sequence, which is homologous to part, or all of the sequence of the mRNA. In constructs, which express the functional protein, the whole of the coding region of the gene is linked to transcriptional control sequences capable of expression in plants.

For example, constructs according to the present invention may be made as follows. A suitable vector containing the desired base sequence for transcription is treated with restriction enzymes to cut the sequence out. The DNA strand so obtained is cloned (if desired, in reverse orientation) into a second vector containing the desired promoter sequence and the desired terminator sequence. Suitable promoters include the Actin2 promoter or the pea plastocyanin promoter sequence. Suitable terminator sequences include that of the *Agrobacterium tumefaciens* nopaline synthase gene (the nos 3' end).

In a DNA construct according to the invention, the transcriptional initiation region may be derived from any plant operative promoter. The transcriptional initiation region may be positioned for transcription of a DNA sequence encoding RNA, which is complementary to a substantial run of bases in a mRNA encoding the desaturase enzyme (making the DNA construct a full or partial antisense construct).

The transcriptional initiation region (or promoter) operative in plants may be a constitutive promoter or an inducible or developmentally regulated promoter, as circumstances require. For example, it may be desirable to modify protein activity at certain stages of the plant's development. Use of a constitutive promoter will tend to affect protein levels and functions in all parts of the plant, while use of a tissue-specific promoter allows more selective control of gene expression and affected functions. Thus the antisense or sense RNA is only produced in the organ in which its action is required.

The DNA constructs of the invention may be inserted into plants to regulate the expression of the gene encoding for a desaturase or thioesterase or other enzymes in the fatty acid pathway resulting in modification of plant characteristics for production of stearic acid or oleic acid or thioesterase activity in the fatty acid synthesis pathway. Depending on the nature of the construct, the production of the gene product may be increased, or reduced, either throughout or at particular stages in the life of the plant. Generally, as would be expected, production of the protein is enhanced only by constructs, which express RNA homologous to the substantially complete endogenous protein mRNAs. Full-length sense constructs may also inhibit protein expression. Constructs containing an incomplete DNA sequence shorter than that corresponding to the complete gene generally inhibit the expression of the gene and production of the proteins, whether they are arranged to express sense or antisense RNA.

A DNA construct of the invention is transformed into a target plant cell. The target plant cell may be part of a whole plant or may be an isolated cell or part of a tissue, which may be regenerated into a whole plant. The target plant cell may be selected from any monocotyledonous or dicotyledonous plant species. The preferred target plant is an oil producing species of monocot or dicot. The more preferred target plant is a Brassica or Helianthus annuus L. Plants may be derived from the transformed plant cell by regeneration of transformants and by production of successive generations of the transformants' progeny.

Constructs according to the invention may be used to transform any plant using any suitable transformation technique to make plants according to the invention. Both monocotyledonous and dicotyledonous plant cells may be transformed in various ways known to the art. In many cases such plant cells (particularly when they are cells of dicotyledonous plants) may be cultured to regenerate whole plants which subsequently reproduce to give successive generations of genetically modified plants. Any suitable method of plant transformation may be used. For example, many dicotyledonous plants such as sunflower, oilseed rape, tomato and melon may be transformed by Agrobacterium Ti plasmid technology, such as described by Bevan (1984, Nucleic Acid Research, 12:8711–8721) or Fillatti et al (Biotechnology, Jul. 1987, 5:726–730). Such transformed plants may be reproduced sexually, or by cell or tissue culture. Other methods use the gene gun, microinjection, PEG and electroporation.

Examples of plants which could be modified to produce the desired oil according to the present invention include the oil from oilseed rape (canola), palm, sunflower, soya. Other possible seed transformants are cereals, for example rice and maize, wheat, barley, oats and rye.

Thus crossing mutants or transgenics or a combination to form seeds containing at least 40% oleic oil and at least 12% stearic oil according to the invention can produce tailor-made seeds and tailor-made oil in accordance with the present invention. The result HSHO lines can be used in further conventional plant improvement practices by crossing with other known or as yet unknown mutant, transgenic or wild type plants.

Alternatively, forming a high stearic line which has a transgene (for example as shown in U.S. Pat. No. 5,443,974) that inhibits stearoyl-ACP desaturase activity can make one of the basic elements of the present invention. The gene can be extracted from sunflower material by using the known Arabidopsis or the Brassica stearoyl-ACP desaturase-encoding gene as taught in U.S. Pat. No. 5,443,974 the sequence of which is in the patent and is incorporated by reference. The known method of transforming sunflower is taught in International application number US97/01419. This application, unfortunately, does not teach a gene; it does teach how to transform the gene once isolated with a plasmid into the plant genome. The teaching of both of these patents together places the transformation of a desaturase gene into a dicot within the ordinary skilled person's ability. Any of these genes or other similar genes having substantial homology can be placed in either the high oleic line or in a HOHT line that is crossed thereto.

The following differences to the standard procedure used to form a transgenic sunflower are herein noted. The preferred method of transformation is the Agrobacterium method of transformation. However, due to gene silencing concerns when sunflower is transformed, the promoter should be either an Arabidopsis actin gene promoter "Actin2", available from the University of Georgia, Life science Building, Athens Ga. 30602–7223 or possibly a pea plastocyanin promoter which is published in the LAST & Gray 1989 (Plant Mol. Biol. 12, 655–666) and in Plant Journal (1993) 3(3):437–49 by K. Pwee and J. Gray supplied by the University of Cambridge Dept. of Plant Science Downing Street Cambridge CB23EA or the like. These promoters are more useful in sunflower transformation than 35S or 19s CaMV promoters, though the pea plastocyanin promoter may still show some difficulties.

Thus a high oleic line with elevated thioesterase activity can be transformed with a gene that produces high stearic acid. Although the thioesterase trait is most often discussed in conjunction with the high oleic line it could also be in the high stearic line that is crossed to the high oleic line to form the HSHO line of the present invention. Alternatively, two lines can be transformed, one to have oleic and one to have higher stearic and they can be crossed to form an inbred which is selected for elevated thioesterase activity and both other traits. Or one line can be transformed with both a high oleic and high stearic gene and selected for based on elevated thioesterase activity.

Alternatively, to avoid transgenic issues a line can be mutated to have both oleic and high stearic with the elevated thioesterase activity in a two step mutation process. Two separate lines can be mutated to carry the oleic and thioesterase trait and the stearic trait and crossed and selfed to form a plant which produces the oil. This would most likely require two inbreds both carrying oleic and stearic oil traits to assure the hybrid formed by crossing these two inbreds had these traits. Once a trait is fixed, through standard breeding or through a marker assisted breeding this trait can readily be moved into different inbreds. By using at least one trait that is transgenic the breeding becomes simpler as transgenes are usually dominant in their inheritance. Thus only one line in a hybrid cross would have to carry the transgene, however, both lines would preferably carry the mutated traits as these are most often recessive or additive traits not dominant traits.

The seed generated when producing the sunflower capable of producing the oil of the present invention is analysed with a methodology described in Garcés, R. and Mancha, M. "One-step lipid extraction and fatty acid methyl esters preparation from fresh plant tissues". Analytical Biochemistry, 211:139–143, 1993. This allows for the detection of seeds with modifications in the composition of any fatty acid. Selected seeds showing a desirably high stearic acid content and/or oleic acid and Vmax of thioesterase activity are selected for further breeding purposes. The seeds are cultivated to the fifth generation to form inbreds that have this inheritable and stable genetic trait.

Sunflower oil having a stearic acid content of at least 12% by weight and a oleic acid content of at least 40% by weight, related to the total amount of fatty acids in the oil, is obtainable from sunflower seeds of the invention in any manner known to the person skilled in the art. The sunflower seeds can be converted to crushed seeds or meal before, during or after the oil extraction process. Such extraction methods are well known and for example one method is described in "Bailey's industrial oil and fat products", Vol. 2, Chapter 3; 4th Edition, John Wiley and Sons, New York (1982). The extraction process preferably used does not involve substantial modification of the oil. The extraction process may be selected to avoid substantial chemical, physical or enzymatic rearrangement with no substantial hardening.

In a further embodiment of the method of the invention, the mutation and selection steps may be followed by conventional plant improvement techniques thus leading to seeds having e.g. an even higher stearic acid content or higher oleic acid or reduced linoleic or altered palmitic by weight, or to seeds having a desirable content of one or more other fatty acids. In still another embodiment the seeds of the invention may be subjected to one or more further mutation treatments or additional transformations.

The sunflower plants may be used in breeding programmes for the development of sunflower lines or hybrids, which programmes are aimed at the production of open pollinated or hybrid varieties meeting the requirements of farming practice regarding yield, disease resistance and other agronomically important traits in major sunflower growing areas in the world. Seeds resulting from these programmes may be used in the growing of commercial sunflower crops.

The invention further relates to sunflower plants produced from seeds according to the invention. Thus, the seeds can be used to produce new parent lines that have high stearic acid content and a high oleic acid content in their oil. These lines should also have an increased thioesterase Vmax as indicated in the definition of high levels of thioesterase on the substrate stearoyl-ACP at 15 DAF. The seeds may be cultured in the normal way on soil or any other substrate. The production of the modified plants does not require very many additional measures as compared to the growing of ordinary sunflower seeds.

The invention also relates to the use in the food industry of sunflower oil extractable from the seeds of the invention. The natural vegetable oil that has been extracted from sunflowers seeds of the present invention has a high stearic acid content between 12 and 35% and at least 40 to 80% oleic acid. This oil can be used directly or it can be combined with other oils, in the production of edible fats or fat mixtures, margarine, vegetable-dairy or in the production of confectionery, cosmetic or bakery goods. The present invention is particularly useful in spreads, sauces, ice cream and soups. The oil is also useful for non-edible products such as lipsticks, soap bars, skin and hair oils, lotions and creams.

In this application the oil of the present invention is interchangeably called oil or fat. The structure of the present invention is in some instances a saturated fatty acid profile that yields a high enough level of saturation to increase the melting point of the oil to make it solid at room temperature. In other saturated fatty acid profiles according to the present invention the material is liquid at room temperature. Both melting points are encompassed by the teachings of the present invention.

This oil is particularly useful in use as a hardstock material for the formation of spreads. This is a fat that has other oils blended into it. In the preferred use the present invention is used as a hardstock at a level of at least 5% depending on the use of the spread the present invention can be used at levels of at least 20%. Higher levels of the present invention can also be employed depending on the traits desired in the resultant spread. The oil may simply replace oils or fats ordinarily used in this type of products. It is within the reach of the skilled person to determine how to use the oil without performing any inventive labor.

A number of food products using the oil of the present invention can be used. These food products would include the present oil at levels from 3% to 100% by weight of the other oils (if any) of food product. The advantage of these oils is that they do not have artificial fatty acid isomers, like the 'trans' isomers found in the hydrogenated oils, and, of course, little to no LLD raising cholesterol, like in the animal fats.

The present invention will be further illustrated by means of the following examples which are given for illustration purposes only and are in no way intended to limit the scope of the invention.

EXAMPLES

The invention also relates to a method for preparing sunflower seeds having an increased stearic acid and oleic acid content as compared to wild type seeds. This method includes the step of treating parent seeds with a mutagenic agent during a period of time and in a concentration sufficient to induce one or more mutations in the genetic trait involved in stearic acid or oleic acid biosynthesis. This results in an increased production of stearic acid and/or an increased level of oleic acid. These mutagenic agents include agents such as sodium azide or an alkylating agent, like ethyl methane sulfonate, of course any other mutagenic agent having the same or similar effects may also be used. The treated seeds will contain inheritable genetic changes. These mutated seeds are then germinated and progeny plants are developed therefrom. To increase the traits in the lines the progeny can be crossed or selfed. The progeny seeds are collected and analysed. Seeds having the HOHT trait or the stearic trait can then be crossed to each other to form the HSHO line. Optionally there can be additional cycles of germination, culturing, and selfing to fix the homozygousity of the traits in the lines and crossing and collection of seeds.

Sodium azide and ethyl methane sulfonate were used as mutagenic agents in Example 1 and 2, respectively. Several sunflower lines with a stearic acid content between 12 and 45% have been obtained. In all these cases the original sunflower parent line for the production of the high stearic acid lines used was RDF-1-532 (Sunflower Collection of Instituto de Agricultura Sostenible, CSIC, Cordoba, Spain) that has from 4 to 7% stearic acid content in the seed oil. The high oleic material used herein is derived from the Russian researched oleic lines. It is sufficient to screen oleic lines for a HOHT and use this line for either transformation or for crossing to a high stearic line to develop a HSHO line. A method for the preparations of the stearic lines, and of oleic lines if necessary, have been described in the following examples.

Example 1

Seeds were mutagenized with a solution of 70 mM of ethyl methane sulfonate (EMS) in water. The treatment was performed at room temperature during 2 hours while shaking (60 rpm). After mutagenesis the EMS solution was discarded and seeds were washed during 16 hours under tap water.

Treated seeds were germinated in the field and plants were self-pollinated. The seeds collected from these plants were used to select new sunflower lines with modifications in the fatty acid composition. By using the method of Garcés, R. and Mancha, M. (supra) the seed fatty acid composition was determined by gas liquid chromatography, after converting the fatty acids into their corresponding methyl esters.

A first plant with 9 to 17% stearic acid content in the oil was selected. The progeny was cultivated for five generations wherein the stearic acid content increased and the new genetic trait became stably fixed in the genetic material of the seed. This line is called CAS-3. The minimum and the maximum stearic acid content of the line were 19 and 35% respectively. The stearic acid content of oil extracted from seeds from this cell line may thus lie between 19 and 35%.

Example 2

Sunflower seeds were mutagenized with sodium azide, at a concentration of 2 mM in water. The treatment was performed at room temperature during two hours while shaking (60 rpm). Then the mutagenesis solution was discarded and seeds were washed during 16 hours with tap water.

Seeds were planted in the field and plants were self-pollinated. Seeds from these plants were collected, and the fatty acid composition was determined by gas liquid chromatography, after converting the fatty acids into their corresponding methyl esters using the method described in Example 1.

Seeds from a plant having around 10% stearic acid in the oil were selected and cultivated for five generations. During this procedure the stearic acid content was increased and the new genetic trait fixed. This line is called CAS-4. A selected sample of this line was analysed resulting in a stearic acid content of 16.1%. The minimum and the maximum values were 12 and 19% respectively.

TABLE 7

| Line | Percentage fatty acids | | | |
| --- | --- | --- | --- | --- |
| | Palmitic | Stearic | Oleic | Linoleic |
| CAS-3 | 5.1 | 26.0 | 13.8 | 55.1 |
| CAS-4 | 5.5 | 16.1 | 24.3 | 54.1 |

Example 3

Sunflower plants were grown from the sunflower seeds of the HOHT line shown in Table 4. Sunflower plants were also grown from the sunflower seeds of CAS-3. The lines were crossed. The plants were assisted by artificial pollination in order to ensure adequate seed production occurred. The F1 seed was produced on the HOHT line, or vice versa, and harvested. The F2 seeds with more than 20% stearate and more than 40% oleate were selected. Although this produces the oil of the present invention the level of production is limited. Therefore fixed inbred lines evidencing seeds with these oil profiles are desirable. These homozygous fixed inbred HSHO lines can then be crossed to form hybrid seed, which will produce F2 seed evidencing the desired oil traits of the present invention. Toward this end the F1 seeds were planted and produced plants were selfed in isolated conditions and F2 seed was produced. The F2 seed was tested for the three traits, high stearic, high oleic and high levels of thioesterase activity. The remaining portion of the seeds evidencing these traits was employed to grow plants to form F3 seed. The selfing and screening and selection process is repeated to develop the fixed homozygous HSHO line, having the following fatty acid profile, C:16 5.4, C:18.0 24.8, C:18.1 58.5, C:18.2 7.2. Once the trait is fixed, similar HSHO lines can cross to form hybrid seed having both traits. According to the invention, sunflower plants and seeds from which said oil can be extracted have been obtained by means of a biotechnological process. This high stearic acid content is an inheritable trait and is fairly independent from the growing conditions.

Example 4

Plants Growth Conditions.

Sunflower (*Helianthus annuus* L.) seeds from high oleic lines used in example 3 with altered seed fatty acid content were used to test for the thioesterase activities over stearoyl-ACP. Plants were cultivated in growth chambers at 25/15° C. (day/night) temperature, 16 hours photoperiod and photon flux density of 300 micromol m-2s-1. Seeds for analysis were harvested at 15 days after flowering and kept at −20° C.

Radioactive Reagents and Preparation of acyl-ACPs.

1–14C-Oleic with specific radioactivity of 2.1 GBq/mmol and [9,10(n)-3H] stearic acid with specific radioactivity of 1.9 GBq/mmol were obtained from American Radiolabeled Chemicals Inc. (St. Louis, Mo., USA). To prepare the fatty acid sodium salt, an appropriate volume of fatty acid solution was transferred to a glass tube, the solvent was removed under a stream of nitrogen, and the residue was dissolved in 10% Triton X-100, 0.6 mM NAOH. This solution was heated at 55° C. for 1 hour to ensure homogeneity. Acyl-ACPs were prepared using a modification of the enzymatic synthesis procedure of Rock C. O., Garwin J. L., Cronan, J. E. Jr. (1981) Preparative enzymatic synthesis of acyl-acyl carrier protein. Methods Enzymology 72:397–403. Assays contained 0.1 M Tris-HCl (pH 8.0), 0.4 M LiCl, 5 mM ATP, 10 mM MgCl2, 2 mM DTT, 130 micron fatty acid sodium salt, 0.27 mM ACP-SH and 1.8 mL of acyl-ACP synthetase (the last two components were purchased from Sigma-Aldrich Quimica S.A. Madrid, Spain) in a final volume of 110 microliter. Reactions were incubated at 37° C. for 3 hours. After this time the pH was acidified to 6.0 by adding 1 microliter of 3.6 M HCl and the mixture was cleaned of free fatty acids using a modification of the method described by Mancha M, Stokes G B, Stumpf P K (1975) Fat metabolism in higher plants. The determination of acyl-acyl carrier protein and acyl coenzyme A in a complex lipid mixture 1,2. Anal. Biochem. 68:600–608. Consisting in adding an equal volume of isopropanol and washing three times with hexane saturated in water/isopropanol (1:1; v/v).

Preparation of Crude Extracts for Enzyme Assays and Protein Determination.

Frozen seeds were peeled and grounded in extract buffer containing 20 mM Tris-HCl (pH 8.5), 2 mM DTT and 5% (v/v) glycerol (Dörmann P, Kridl J C, Ohlrogge J B (1994)

Cloning and expression in *Escherichia coli* of a cDNA coding for the oleoyl-acyl carrier protein thioesterase from coriander (*Coriandrum sativum L.*). Biochim. Biophys. Acta 1212:134–136) at 1 g of tissues/10 ml of buffer. Protein concentrations were measured using a Protein Assay Kit (Bio-Rad) according to the manufacturer's recommendations, with BSA as standard.

Enzyme Assays.

Acyl-ACP thioesterase activity was assayed in a final volume of 170 microliter using 130 microliter of crude extract. Control assays had crude extract omitted. Reactions mixtures contained 20 mM Tris-HCl (pH 8.5), 5% glycerol and 2 mM dithiothreitol (DTT) and different concentrations of substrates (stearoyl-ACP and oleoyl-ACP). Incubations were carried out for 20 min at 25° C. Reactions were stopped by the addition of 170 microliter of 1 M acetic acid in isopropanol containing 1 mM of oleic acid. Mixtures were then washed three times with hexane saturated in water/isopropanol (1:1, v/v). Acyl-ACP thioesterase activity was determined by counting the radioactivity of the aqueous phase, which contained the non-hydrolysed substrates. Then, 3 ml of solvent scintillant (purchased from National Diagnostics, Hessle, England) was added and the radioactivity was measured using a scintillation counter (Rackbeta II; LKB, Sweden). Data from acyl-ACP thioesterase assays were fitted to the Michaelis-Menten equation by non-linear least-squares regression analysis using Microcal Origin 4.1, and correlated to $P<0.05$, as determined by paired Student's test. Vmax and Km were derived from these curves.

REFERENCES

1 Jones, A., Davies, H. M. and Voelker, T. A.(1995) Plant Cell 7, 359–371
2 Gibson, S., Falcone, D. L., Browse, J. and Somerville, C. R. (1994) Plant Cell Environ 17, 627–637
3 Dormann, P., Spener, F. and Ohlrogge, J. B. (1993) Planta 189, 425–432
4 Dormann, P., Voelker, T. A. and Ohlrogge, J. B. (1995) Arch. Biochem. Biophys. Res. Commun. 316, 612–618
5 Hawkins, D. J. and Kridi, J. (1998) Plant J. 13, 743–752
6 Voelker, T. A., Worrell, A. C., Anderson, L., Bleibaum, J., Fan, C., Hawkins, D. J., Radke, S. E. and Davies, H. M. (1992) Science 257, 72–74
7 Eccleston, V. S., Cranmer, A. M., Voelker, T. A. and Ohlrogge, J. B. (1996) Planta 198, 46–53
8 Davies, H. M. (1993) Phytochem. 33, 1353–1356
9 Griffiths, G., Walsh, M. C. and Harwood, J. L. (1993) Phytochem. 32, 1403–1405
10 Fuhrmann, J., and Heise, K. P. (1993) Z. Naturforsch 48, 616–622
11 Dehesh, K., Edwards, P., Hayes, T., Cranmer, A. M. and Fillatti, J. (1996) Plant Physiol. 110, 203–210
12 Voelker, T. A., Jones, A., Cranmer, A. M., Davies, H. M., and Knutzon, D. S. (1997) Plant Physiol. 114, 669–677
13 Segel, I. H. (1975) in Enzyme Kinetics, pp. 113–118, John Wiley and Sons, Inc., New York
14 Hara, A. and Radin, N. S. (1978) Anal. Biochem. 90, 420–426
15 Garcés, R. and Mancha, M. (1993) Anal. Biochem. 211, 139–143
16 Rock, C. O., Garwin, J. L. and Cronan, J. E. Jr. (1981) Meth. Enzymol. 72, 397–403
17 Mancha, M., Stokes, G. B. and Stumpf, P. K. (1975) Anal. Biochem. 68, 600–608
18 Dormann, P., Frentzen, M. and Ohirogge, J. B. (1994) Plant Physiol. 104, 839–844
19 Ohlrogge, J. B., Shine, W. E. and Stumpf, P. K. (1978) Arch. Biochem. Biophys. Res. Commun. 189, 382–391
20 Knutzon, D S., Thompson, G. A., Radke, S. E., Johnson, W. B., Knauf, V. C. and Kridl, J. C. (1992) Proc. Nat'l Aca., Sci. USA 89:2624–28
21 Hellyer, A., Leadlay, P. F. and Slabas, A. R. (1992) Plant Mol. Biol. 20, 763–780
22 Liu, D. and Post-Beittenmiller, D. (1995) J. Biol. Chem. 270, 16962–16969
23 Roughan, P. G. and Ohirogge, J. B. (1996) Plant Physiol. 110, 1239–1247
24 Mckeon, T. A. and Stumpf, P. K. (1982) J. Biol. Chem. 257, 12141–12147
25 Yadav, N., Wierzbicki, A., Knowlton, S., Pierce, J., Ripp, K., Hitz, W., Aegerter, M. and Browse, J. (1993) in Current Topics in Plant Physiology (Murata, N. and Somerville, C. R., eds.), pp. 60–66, American Society of Plant Physiologists, Rockville, Md.

We claim:

1. Sunflower meal comprising oil having an oleic acid content of more than 40 wt % based on the total fatty acid content of said oil and a stearic acid content of more than 12 wt % based on the total fatty acid content of said oil.

2. A sunflower meal of claim 1, wherein the oleic acid content of the oil is from 55 to 75 wt.

3. A sunflower meal of claim 1, wherein the stearic acid content of the oil is from 15 to 40 wt %.

4. A sunflower meal of claim 1, wherein the oil comprises a total level of saturated fatty acids of at least 20 wt %.

5. A sunflower meal of claim 1, wherein the oil comprises a linoleic acid content of less than 20 wt %.

6. A sunflower meal of claim 1, wherein from 95 to 100 w/w % of the saturated fatty acid groups of the oil are in the 1 or 3 position.

* * * * *

UNITED STATES PATENT AND TRADEMARK OFFICE
CERTIFICATE OF CORRECTION

PATENT NO. : 7,141,267 B2 Page 1 of 2
APPLICATION NO. : 10/607803
DATED : November 28, 2006
INVENTOR(S) : E. Martinez Force et al.

It is certified that error appears in the above-identified patent and that said Letters Patent is hereby corrected as shown below:

| COLUMN | LINE | ERROR |
|---|---|---|
| Title Page (56) Pg. 2, col. 2 | Refs. Cited (Other Publs., Item 16) | "*46*99):3577-3582," should read --*46*(9):3577-3582,-- |
| Specification: | | |
| 2 | 39 | "35:739-42(1995)." should read --35:739-42 (1995).-- |
| 3 | 19 | after "to say" delete ";" |
| 3 | 24 | "ojiseeds" should read --oilseeds-- |
| 5 | 12 | "22;0" should read --22:0-- |
| 9 | 20 | "selected-after" should read --selected after-- |
| 11 | 21 | "stearoyl-ACP(HOLT)" should read --stearoyl-ACP (HOLT)-- |
| 11 | 22 | "stearoyl-ACP(HOHT)" should read --stearoyl-ACP (HOHT)-- |
| 20 | 48 | "micron" should read --microM-- |
| 20 | 49 | "mL" should read --mU-- |
| 22 | 25 | "Ohirogge," should read --Ohlrogge,-- |

UNITED STATES PATENT AND TRADEMARK OFFICE
CERTIFICATE OF CORRECTION

PATENT NO. : 7,141,267 B2
APPLICATION NO. : 10/607803
DATED : November 28, 2006
INVENTOR(S) : E. Martinez Force et al.

It is certified that error appears in the above-identified patent and that said Letters Patent is hereby corrected as shown below:

| COLUMN | LINE | ERROR |
|---|---|---|
| 22 (Claim 2, line 2) | 42 | "75 wt." should read --75 wt %.-- |

Signed and Sealed this

Eighth Day of May, 2007

JON W. DUDAS
*Director of the United States Patent and Trademark Office*